(12) United States Patent
Jadhav

(10) Patent No.: US 6,368,346 B1
(45) Date of Patent: Apr. 9, 2002

(54) BIORESORBABLE STENT

(75) Inventor: Balkrishna S. Jadhav, Plymouth, MN (US)

(73) Assignee: American Medical Systems, Inc., Minnetonka, MN (US)

(*) Notice: Subject to any disclaimer, the term of this patent is extended or adjusted under 35 U.S.C. 154(b) by 0 days.

(21) Appl. No.: 09/324,743

(22) Filed: Jun. 3, 1999

(51) Int. Cl.[7] ............... A61F 2/06; D01D 5/12
(52) U.S. Cl. ................... 623/1.22; 264/210.8
(58) Field of Search ............ 623/11.11, 16.11, 623/23.64, 23.75, 1.1, 1.22, 1.33, 1.38, 1.49, 1, 1.5, 1.51, 1.54; 264/210.8; 424/422–425

(56) References Cited

U.S. PATENT DOCUMENTS

| | | |
|---|---|---|
| 3,797,499 A | 3/1974 | Schneider |
| 4,610,688 A | 9/1986 | Silvestrini et al. |
| 4,655,771 A | 4/1987 | Wallsten |
| 4,834,755 A | 5/1989 | Silvestrini et al. |
| 4,968,317 A | 11/1990 | Tormala et al. |
| 5,085,629 A | 2/1992 | Goldberg et al. |
| 5,147,400 A | 9/1992 | Kaplan et al. |
| 5,160,341 A | 11/1992 | Brenneman et al. |
| 5,171,262 A | 12/1992 | MacGregor |
| 5,236,447 A | 8/1993 | Kubo et al. |
| 5,342,348 A | 8/1994 | Kaplan |
| 5,419,760 A | 5/1995 | Narcisco, Jr. |
| 5,423,885 A | 6/1995 | Williams |
| 5,425,739 A | 6/1995 | Jessen |
| 5,441,515 A | 8/1995 | Khosravi et al. |
| 5,443,458 A | 8/1995 | Eury |
| 5,545,208 A | 8/1996 | Wolff et al. |
| 5,601,591 A | 2/1997 | Edwards et al. |
| 5,629,077 A | 5/1997 | Turnlund et al. |
| 5,713,947 A | 2/1998 | Davidson |
| 5,766,710 A | 6/1998 | Turnlund et al. |
| 5,876,432 A | 3/1999 | Lau et al. |
| 5,906,641 A | 5/1999 | Thompson et al. |
| 5,957,974 A | 9/1999 | Thompson et al. |
| 6,045,568 A | 4/2000 | Igaki et al. |
| 6,123,722 A | 9/2000 | Fogarty et al. |
| 6,165,486 A * | 12/2000 | Marra et al. ............. 424/423 |

FOREIGN PATENT DOCUMENTS

| | | |
|---|---|---|
| EP | 0 895 762 A2 | 2/1999 |
| WO | WO88/08813 | 2/1988 |
| WO | WO89/00031 | 1/1989 |
| WO | WO90/04982 | 5/1990 |
| WO | WO91/17789 | 11/1991 |
| WO | WO92/16166 | 10/1992 |
| WO | WO95/17859 | 7/1995 |
| WO | WO97/49353 | 12/1997 |
| WO | WO99/55256 | 11/1999 |
| WO | WO00/00105 | 1/2000 |
| WO | WO00/44306 | 8/2000 |
| WO | WO00/44308 | 8/2000 |

* cited by examiner

*Primary Examiner*—David J. Isabella
(74) *Attorney, Agent, or Firm*—Oppenheimer Wolff & Donnelly LLP

(57) ABSTRACT

A bio-compatible and bioresorbable stent is disclosed that is intended to restore or maintain patency following surgical procedures, traumatic injury or stricture formation. The stent is composed of a blend of at least two polymers that is either extruded as a monofilament then woven into a braid-like embodiment, or injection molded or extruded as a tube with fenestrations in the wall. Methods for manufacturing the stent are also disclosed.

13 Claims, 8 Drawing Sheets

BIORESORBABLE STENT

FIELD OF THE INVENTION

This invention relates to stents, and particularly to bioresorbable stents useful in the treatment of strictures and preventing restenosis disorders.

BACKGROUND

Tubular organs and structures such as blood vessels, the esophagus, intestines, endocrine gland ducts and the urethra are all subject to strictures i.e., a narrowing or occlusion of the lumen. Strictures can be caused by a variety of traumatic or organic disorders and symptoms can range from mild irritation and discomfort to paralysis and death. Treatment is site specific and varies with the nature and extent of the occlusion.

Life threatening stenoses are most commonly associated with the cardiovascular system and are often treated using percutaneous transluminal coronary angioplasty (PTCA). This process reduces the stricture by expanding the artery's diameter at the blockage site using a balloon catheter. However, three to six months after PTCA, approximately 30% to 40% of patients experience restenosis. Injury to the arterial wall during PTCA is believed to be the initiating event causing restenosis and primarily results from vascular smooth muscle cell proliferation and extracellular matrix secretion at the injured site. Restenosis is also a major problem in non-coronary artery disease including the carotid, femoral, iliac, popliteal and renal arteries.

Stenosis of non-vascular tubular structures is often caused by inflammation, neoplasm and benign intimal hyperplasia. In the case of esophageal and intestinal strictures, the obstruction can be surgically removed and the lumen repaired by anastomosis. The smaller transluminal spaces associated with ducts and vessels may also be repaired in this fashion; however, restenosis caused by intimal hyperplasia is common. Furthermore, dehiscence is also frequently associated with anastomosis requiring additional surgery which can result in increased tissue damage, inflammation and scar tissue development leading to restenosis.

Problems with diminished urine flow rates are common in aging males. The most frequent cause is benign prostatic hypertrophy (BPH). In this disease the internal lobes of the prostate slowly enlarge and progressively occlude the urethral lumen. A number of therapeutic options are available for treating BPH. These include watchful waiting (no treatment), several drugs, a variety of so-called "less invasive" therapies, and transurethral resection of the prostate (TURP)—long considered the gold standard.

Urethral strictures are also a significant cause of reduced urine flow rates. In general, a urethral stricture is a circumferential band of fibrous scar tissue which progressively contracts and narrows the urethral lumen. Strictures of this type may be congenital or may result from urethral trauma or disease. Strictures were traditionally treated by dilation with sounds or bougies. More recently, balloon catheters became available for dilation. Surgical urethrotomy is currently the preferred treatment, but restenosis remains a significant problem.

Recent advances in biomedical engineering have led to the development of stenting i.e., mechanical scaffolding, to prevent restenosis and keep the previously occluded lumens open. There are two general types of stents: permanent and temporary. Temporary stents can be further subdivided into removable and absorbable.

Permanent stents are used where long term structural support or restenosis prevention is required, or in cases where surgical removal of the implanted stent is impractical. Permanent stents are usually made from metals such as Phynox, 316 stainless steel, MP35N alloy, and superelastic Nitinol (nickel-titanium).

Stents are also used as temporary devices to prevent closure of a recently opened urethra following minimally invasive procedures for BPH which typically elicit post treatment edema and urethral obstruction. In these cases, the stent will typically not be covered with tissue (epithelialized) prior to removal.

Temporary absorbable stents can be made from a wide range of synthetic bio-compatible polymers depending on the physical qualities desired. Representative biocompatible polymers include polyanhydrides, polycaprolactone, polyglycolic acid, poly-L-lactic acid, poly-D-L-lactic acid and polyphosphate esters.

Stents are designed to be deployed and expanded in different ways. A stent can be designed to self expand upon release from its delivery system, or it may require application of a radial force through the delivery system to expand the stent to the desired diameter. Self expanding stents are typically made of metal and are woven or wound like a spring. Synthetic polymer stents of this type are also known in the art. Self-expanding stents are compressed prior to insertion into the delivery device and released by the practitioner when correctly positioned within the stricture site. After release, the stent self expands to a predetermined diameter and is held in place by the expansion force or other physical features of the device.

Stents which require mechanical expansion by the surgeon are commonly deployed by a balloon-type catheter. Once positioned within the stricture, the stent is expanded in situ to a size sufficient to fill the lumen and prevent restenosis. Various designs and other means of expansion have also been developed. One variation is described in Healy and Dorfman, U.S. Pat. No. 5,670,161. Healy and Dorfman disclose the use of a bio-compatible stent that is expanded by a thermo-mechanical process concomitant with deployment.

Approximately one-third of all patients undergoing surgery, catheterization or balloon dilation to repair bulbar urethral strictures experience restenosis. In these patients the use of urethral stents has provided satisfactory relief from symptoms. (Badlani, G. H., et al., *UroLume® Endourethral Prosthesis for the Treatment of Urethral Stricture Disease: Long-term Results of the North American Multicenter UroLume®* Trial. Urology: 45:5, 1993). Currently, urethral stents are composed of bio-compatible metals woven into a tubular mesh or wound into a continuous coil and are inserted endoscopically after opening the stricture by urethrotomy or sequential dilation. The stent is initially anchored in place through radial force as the stent exerts expansion pressure against the urethral wall. With woven stents epithelial cells lining the urethra begin to grow through the stent's open weave between six and 12 weeks after insertion, thereby permanently securing the stent.

For most patients this is a one time process without complication. However, some men experience post insertion complications including stent migration, excessive epithelialization, and stent encrustation. In some cases excessive epithelial tissue may be resected transurethrally. In other situations stent removal may be necessary. Depending on the condition of the stent, removal procedures range from a relatively simple transurethral procedure to open surgery with excision and urethroplasty. All complications increase patent discomfort and health care costs.

Recently, a number of bio-compatible, bioresorbable materials have been used in stent development and in situ drug delivery development. Examples include U.S. Pat. No. 5,670,161 (a thermo-mechanically expanded biodegradable stent made from a co-polymer of L-lactide and ϵ-caprolactone), U.S. Pat. No. 5,085,629 (a bioresorbable urethral stent comprising a terpolymer of L-lactide, glycolide and ϵ-caprolactone) U.S. Pat. No. 5,160,341 (a resorbable urethral stent made from polylactic acid or polyglycolic acid), and U.S. Pat. No. 5,441,515 (a bio-erodible drug delivery stent and method with a drug release layer).

The bioresorbable stents discussed in these earlier references are all designed and made from co-polymers, which is in sharp contrast to the use of the blending process of the present invention. The blending aspect of the present invention overcomes disadvantages associated with the prior art co-polymers insofar as it is more cost effective than co-polymerization, which typically must be out-sourced by end product stent manufacturers. The blending process also offers greater versatility insofar as the raw materials used in earlier co-polymeric stents were fixed in design and physical qualities. Any changes in the polymer formulation necessary to improve stent performance using a co-polymerization process can only be accomplished by having new co-polymer materials manufactured by the supplier. This often results in excessive delays in product development and significantly increases research and development costs.

Furthermore, co-polymers of L-lactide and ϵ caprolactone are typically mostly amorphous and may be more susceptible to hydrolytic decomposition than a blend of poly-L-lactide and poly-ϵ-caprolactone of similar composition. Additionally, it is more difficult to maintain consistency in the manufacture of co-polymers than homopolymers, resulting in significant batch to batch variation in copolymers.

Consequently, there remains a need for a self expanding stent with stable and predictable physical characteristics suited for a wide variety of physiological conditions. In particular, there is a need for a stent making process and stent design that can be easily and cost effectively implemented for any number of application requirements.

SUMMARY

It is an object of the present invention to provide a blended polymeric stent providing short to intermediate-term functional life in vivo.

It is another objective of the invention to provide a medical device that remains bio-compatible during prolonged intimate contact with human tissue and is fully bioresorbable, thus eliminating the need for costly, painful and potentially damaging post insertion removal.

Furthermore, it is another object of the present invention to provide a medical device that will temporarily restore, or maintain patency of the male urethra while permitting voluntary urination, thereby liberating the patient from catheterization, permitting voluntary urination, and reducing the risk of catheter associated urinary tract infections.

These and other objectives not specifically enumerated here are addressed by a self expanding, bioresorable stent and stent making process in accordance with the present invention, which stent may include a tubular-shaped member having first and second ends and a walled surface disposed between the first and second ends. The walled surface may include a substantially helical-shape of woven monofilaments wherein the monofilaments are composed of a blend of bioresorbable, bio-compatible polymers.

Another embodiment of the present invention may include a bioresorbable stent having a radially self expanding, tubular shaped member which may also expand and contract along its horizontal axis (axially retractable). The stent having first and second ends and a walled surface disposed between the first and second ends. The walled surface may include a plurality of substantially parallel pairs of monofilaments 14 with the substantially parallel pairs of monofilaments woven in a helical shape. The stent is woven such that one-half of the substantially parallel pairs of monofilaments are wound clockwise in the longitudinal direction and one-half of the substantially parallel pairs of monofilaments are wound counterclockwise in the longitudinal direction. This results in a stent having an alternating, over-under plait of the oppositely wound pairs of monofilaments.

Still another embodiment of the present invention may include a radially expandable, axially retractable bioresorbable stent made from a blend of at least two bio-compatible, bioresorbable polymers injection molded into a substantially tubular shaped device. The injection molded or extruded tubular shape device may have first and second ends with a walled structure disposed between the first and second ends and wherein the walled structure has fenestrations therein.

According to another aspect of the invention, a method for producing a stent may include blending at least two bioresorbable, bio-compatible polymers in a predetermined ratio to form a blend and producing a monofilament from the blend by an extrusion process. The monofilament may have a diameter between approximately 0.145 mm and 0.6 mm. The monofilaments may be extruded to a draw ratio of between approximately 3.5 to 5.5, preferably about 4.5. The monofilaments may be braided into a substantially tubular device. Then the tubular device may be annealed at a temperature between the glass transition temperature and melting temperature of the blended polymers for between five minutes and 18 hours.

Additional objects and advantages of the present invention and methods of construction of same will become readily apparent to those skilled in the art from the following detailed description, wherein only the preferred embodiments are shown and described, simply by way of illustration of the best mode contemplated of carrying out the invention. As will be realized, the invention is capable of modification in various respects, all without departing from the invention. Accordingly, the drawings and description are to be regarded as illustrative in nature, and not as restrictive.

BRIEF DESCRIPTION OF THE DRAWINGS

A detailed description of the invention is hereafter described by non-limiting examples with specific reference being made to the drawings in which.

DETAILED DESCRIPTION

Figure 1:
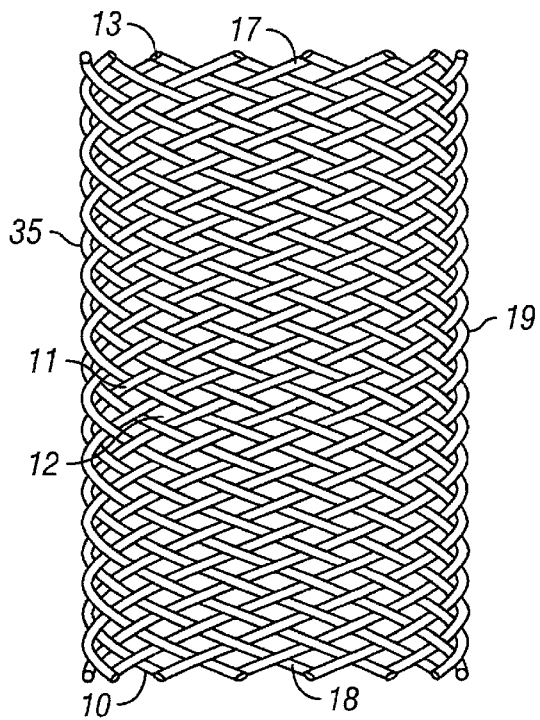
FIG. 1 depicts a 30 strand version of the bioresorbable stent in accordance with a preferred embodiment of the present invention.

A bioresorbable stent 10, 14, in accordance with a first embodiment of the present invention comprises either woven monofilaments (FIGS. 1 and 2) or, in a second embodiment 23 an injection molded or extruded fenestrated tube (FIG. 3) formed from blends of at least two bioresorbable, bio-compatible polymers. These polymers may include, but are not limited to poly-L-lactide (PLLA), poly-D,L-lactide (PDLA) and poly-ε-caprolactone (PCL). A preferred polymeric substrate is made by blending PLLA and PCL.

This stent 10, 14, 23 is used for temporary obstruction relief associated with various disease conditions of the bulbar, membranous or prostatic urethra. Moreover, the stent 10, 14, 23 is designed to be self-expanding and can be formulated to have different nominal functional lives. As the urothelium covered stent 10, 14, 23 reaches the end of its usable life, it is slowly absorbed into the surrounding tissues and metabolized via the tricarboxylic acid cycle and is excreted as carbon dioxide and water. If the stent 10, 14, 23 remains uncovered by urothelium, it will slowly disintegrate and be excreted in the urine flow.

In the first embodiment the stent 10, 14 is a tubular shaped member having first and second ends 17, 18, 17', 18' and a walled surface 19, 19' disposed between the first and second ends 17, 18, 17', 18'. The walls are composed of extruded polymer monofilaments woven into a braid-like embodiment. In the second embodiment, the stent 23 is injection molded or extruded. Fenestrations 24 are molded, laser cut, die cut, or machined in the wall of the tube.

The stent 10, 14, 23 is provided as a sterile device that is compressed to a first diameter of between approximately 6 mm to 10 mm and inserted into a reusable delivery tool (not shown) in the operating room immediately before implantation. Once the stent 10, 14, 23 is deployed, it self expands outwardly to a variable second diameter conforming to the lumen. The size of the lumen together with the elasticity and circumferential pressure of the surrounding tissues determine the stent's final nominal diameter. The stents' non-compressed, or resting state, diameter, is between approximately 12 mm to 18 mm.

Figure 4:
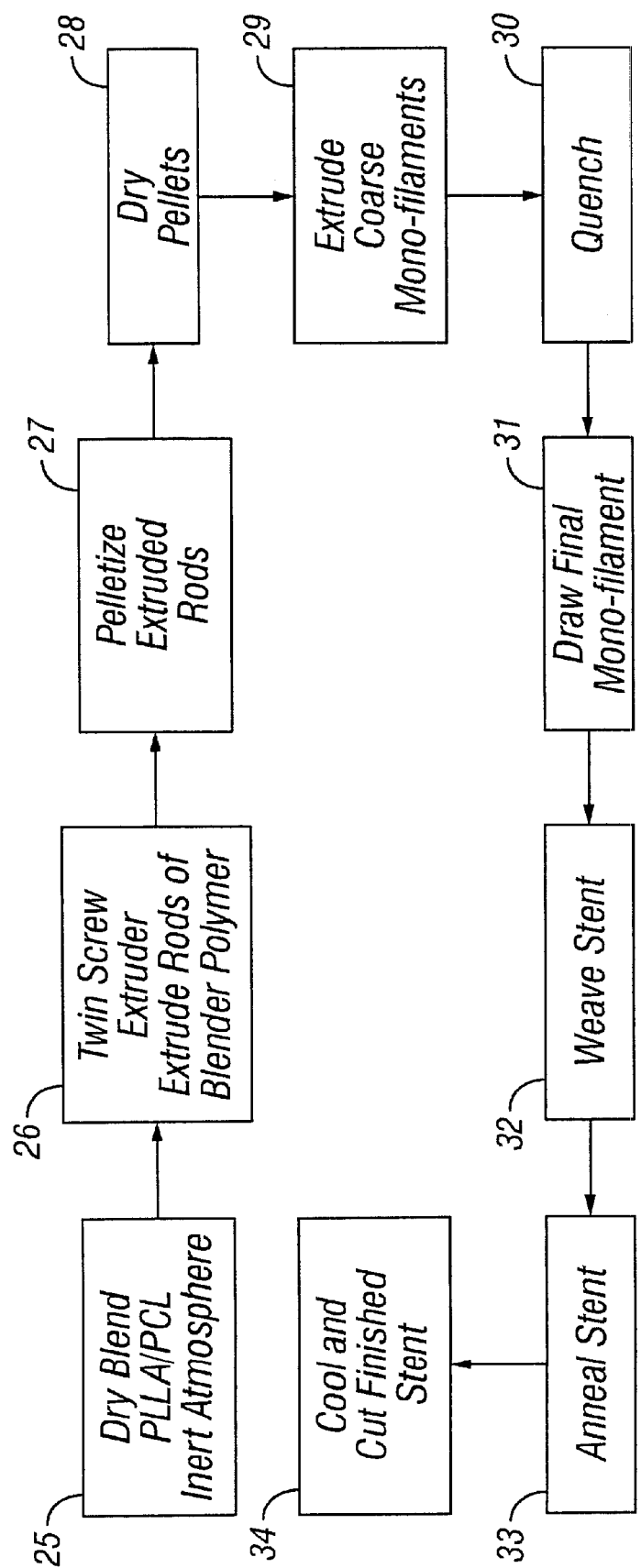
FIG. 4 diagramatically depicts the manufacturing method of the first embodiment of the present invention.

The method for formulation of the stent 10, 14 will now be described (FIG. 4). The PLLA and PCL polymers are first dry blended 25 under an inert atmosphere, then extruded in a rod form 26. In a preferred embodiment of the present invention, granules of PLLA and PCL are dry-blended with a PLLA/PCL ratio of between approximately 80:20 to 99:1, preferably 90:10.

The blended PLLA and PCL polymer rod is pelletized 27 then dried 28. The dried polymer pellets are then extruded 29 forming a coarse monofilament which is quenched 30. The extruded, quenched, crude monofilament is then drawn into a final monofilament 31 with an average diameter from approximately 0.145 mm to 0.6 mm, preferably between approximately 0.35 mm and 0.45 mm. Approximately 10 to approximately 50 of the final monofilaments 31 are then woven 32 in a plaited fashion with a braid angle 12, 16 from about 100 to 150 degrees on a braid mandrel of about 3 mm to about 30 mm in diameter. The plaited stent 10, 14 is then removed from the braid mandrel and disposed onto an annealing mandrel having an outer diameter of equal to or less than the braid mandrel diameter and annealed 33 at a temperature between about the polymer-glass transition temperature and the melting temperature of the polymer blend for a time period between about five minutes and about 18 hours in air, an inert atmosphere or under vacuum. The stent 10, 14 is then allowed to cool and is then cut 34.

Figure 5:
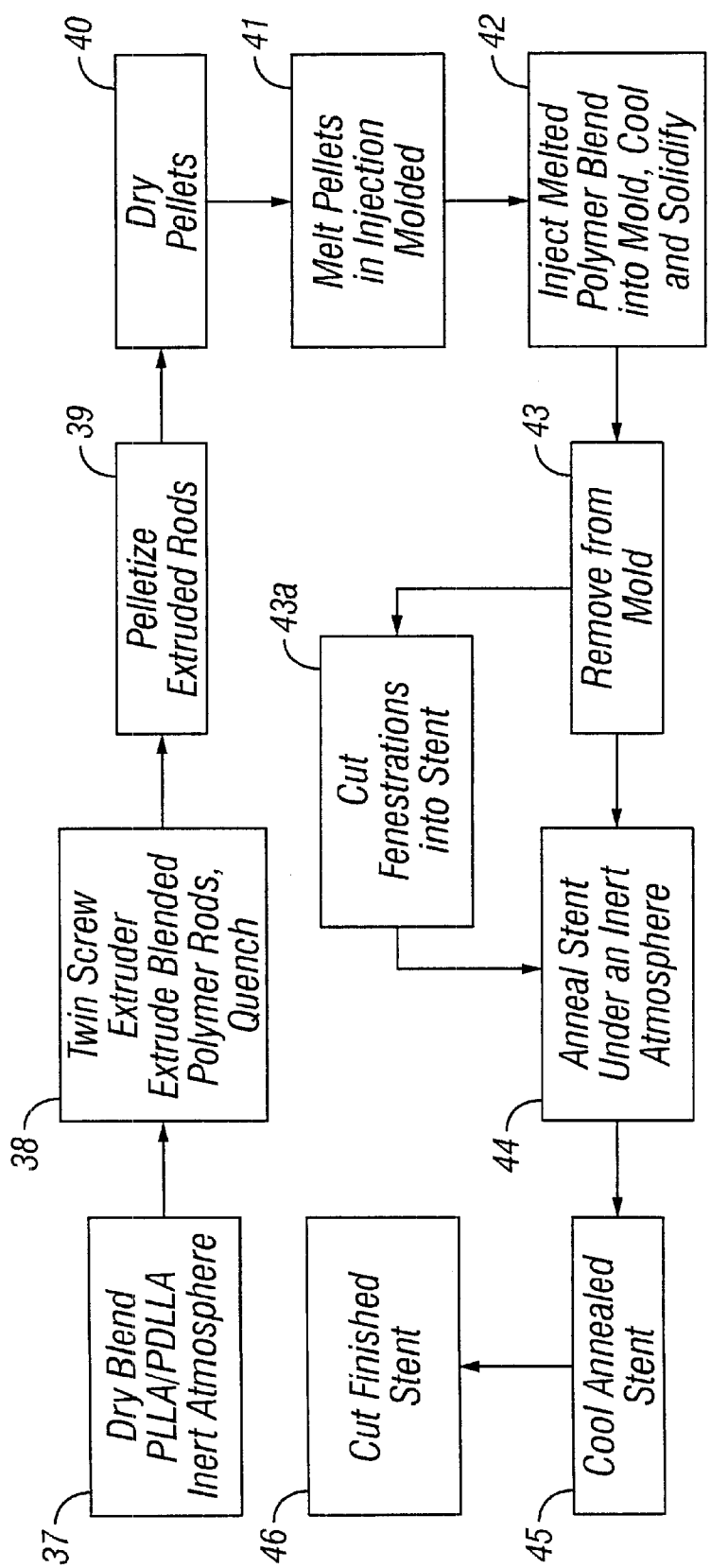
FIG. 5 diagramatically depicts the manufacturing method of the second embodiment of the present invention.

The manufacturing flow chart of stent 23 is presented in FIG. 5. In the first step 37 a blend is made of PLLA and PDLLA in a ratio of between approximately 50:50 to 70:30, preferable 60:40. The blending is done in an inert atmosphere or under vacuum. The blended PLLA and PDLLA is extruded in rod form 38, quenched 38, then pelletized 39. Typically, the polymer pellets are dried 40, then melted in the barrel of an injection molding machine 41 and then injected into a mold under pressure where it is allowed to cool and solidify 42. The stent is then removed from the mold 43. The stent tube may, or may not, be molded with fenestrations in the stent tube.

In a preferred embodiment of the fenestrated stent 23 the tube blank is injection molded or extruded, preferably injection molded, without fenestrations. After cooling, fenestrations are cut into the tube using die-cutting, machining or laser cutting, preferably laser cutting 43a. The resulting fenestrations, or windows, may assume any shape which does not adversely affect the compression and self-expansion characteristics of the final stent.

The stent is then disposed on an annealing mandrel 44 having an outer diameter of equal to or less than the innner diameter of the stent and annealed at a temperature between about the polymer-glass transition temperature and the melting temperature of the polymer blend for a time period between about five minutes and 18 hours in air, an inert atmosphere or under vacuum 44. The stent 23 is allowed to cool 45 and then cut as required 46.

The blends of PCL, PLLA, and PDLLA made in accordance with the present invention have been found to provide improved processability and stability versus a co-polymerization process. Without intending to be bound by this theory, one possible explanation for the improvements can be attributed to the difference in physical states in which the individual polymers exist once combined. Typically, co-polymers are mostly amorphous compositions, but blends of PLLA and PCL may exist as different size semicrystalline domains of each polymer with a greater percentage of PCL at the surface. Morphology of both domains may be manipulated by thermal treatments. This increased concentration of PCL at the surface is believed to contribute to the blended composition's increased resistance to hydrolytic attack. Control over the morphology of the final polymer blend is an advantage to providing the improved physical and biological properties of the stent.

The stent's 10, 14, 23 mechanical properties and strength generally increase proportionally with the molecular weight of the polymers used. The optimum molecular weight range is selected to accommodate processing effects and yield a stent with desired mechanical properties and in vivo degradation rate. The preferred PLLA raw material of the stent 10, 14, 23 should have an inherent viscosity of approximately $\geq 4.5$ dl/g (preferably $\geq 8.0$ dl/g) and a number average molecular weight of approximately 450,000 daltons or greater (preferably $\geq 750,000$ daltons). The preferred PCL raw material of the stent 10, 14, should have an inherent viscosity of approximately $\geq 1.6$ dl/g (preferably $\geq 3.0$ dl/g) and a number average molecular weight of approximately 100,000 daltons or greater (preferably $\geq 200,00$ daltons). The preferred PDLLA raw material should have an inherent viscosity of $\geq 3.0$ dl/g (preferably $\geq 5.0$ dl/g) and a number average molecular weight of approximately 100,000 daltons or greater (preferably $\geq 500,000$ daltons). Inherent viscosity is determined under the following standard conditions: 0.1% solution in chloroform at 25° C. using a Cannon-Fenske capillary viscometer.

Two physical qualities of the polymer or polymer blend used to fabricate the stent 10, 14, 23 play important roles in defining the overall mechanical qualities of the stent 10, 14, 23: tensile strength and tensile modulus. Tensile strength is defined as the force per unit area at the breaking point. It is the amount of force, usually expressed in pounds per square inch (psi), that a substrate can withstand before it breaks, or fractures. The tensile modulus, expressed in psi, is the force required to achieve one unit of strain which is an expression of a substrate's stiffness, or resistance to stretching, and relates directly to a stent's self-expansion properties.

The PLLA and PCL blend in the woven embodiment possesses a tensile strength in the range from about 40,000 psi to about 120,000 psi with an optimum tensile strength for the stent 10, 14, of approximately between 60,000 to 120,000 psi. The tensile strength for the fenestrated stent 23 is from about 8,000 psi to about 12,000 psi with an optimum of about 8,700 psi to about 11,600 psi. The tensile modulus of polymer blends in both embodiments ranges between approximately 400,000 psi to about 2,000,000 psi. The optimum range for a stent application in accordance with the present invention is between approximately 700,000 psi to approximately 1,200,000 psi for the woven embodiment and approximately 400,000 psi to 800,000 psi for the fenestrated embodiment.

In one embodiment, thirty spools are wound with monofilament and a 30 strand braid is prepared (FIG. 1). The monofilaments 35 are interwoven in a helical pattern on a round bar mandrel such that one-half of the monofilaments are wound clockwise. Each monofilament intersects 11 the oppositely wound monofilaments in an alternating over-under pattern such that a tubular braid is made with crossing angles 12 between overlapping monofilaments in the longitudinal or axial direction (when the stent 10 is in a non-compressed, resting position) of 100–150 degrees. The braided device is transferred to an annealing mandrel having a diameter equal to or less than the round braiding mandrel. The ends 13 of the braid are compressed or extended to yield the optimum post annealing geometry; then the ends are secured to the annealing mandrel. The device is then annealed by heating the annealing bar and stent to 90° C. for one hour in an inert atmosphere followed by a second heating cycle for 2 hours at 140° C. in the same inert atmosphere. The stent is not allowed to cool between heating cycles. Finally, the stent is cooled, removed from the annealing bar and cut to the desired length. FIG. 4 diagramatically depicts this process.

Figure 2:
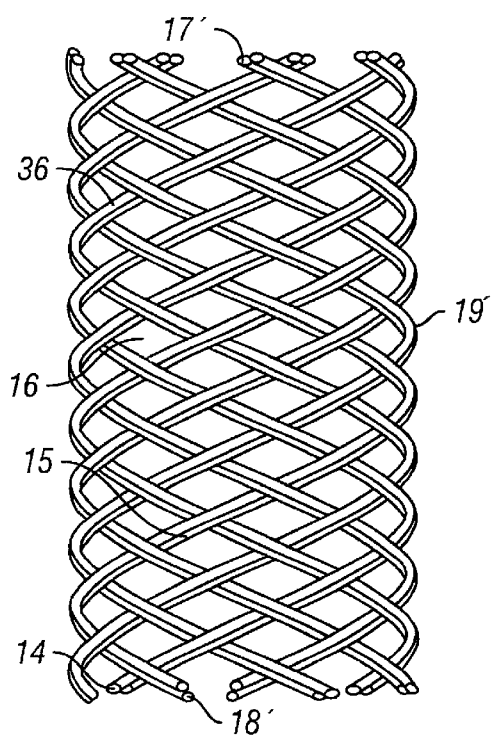
FIG. 2 depicts a 48 strand version of the bioresorbable stent in accordance with a preferred embodiment of the present invention.
Figure 3:
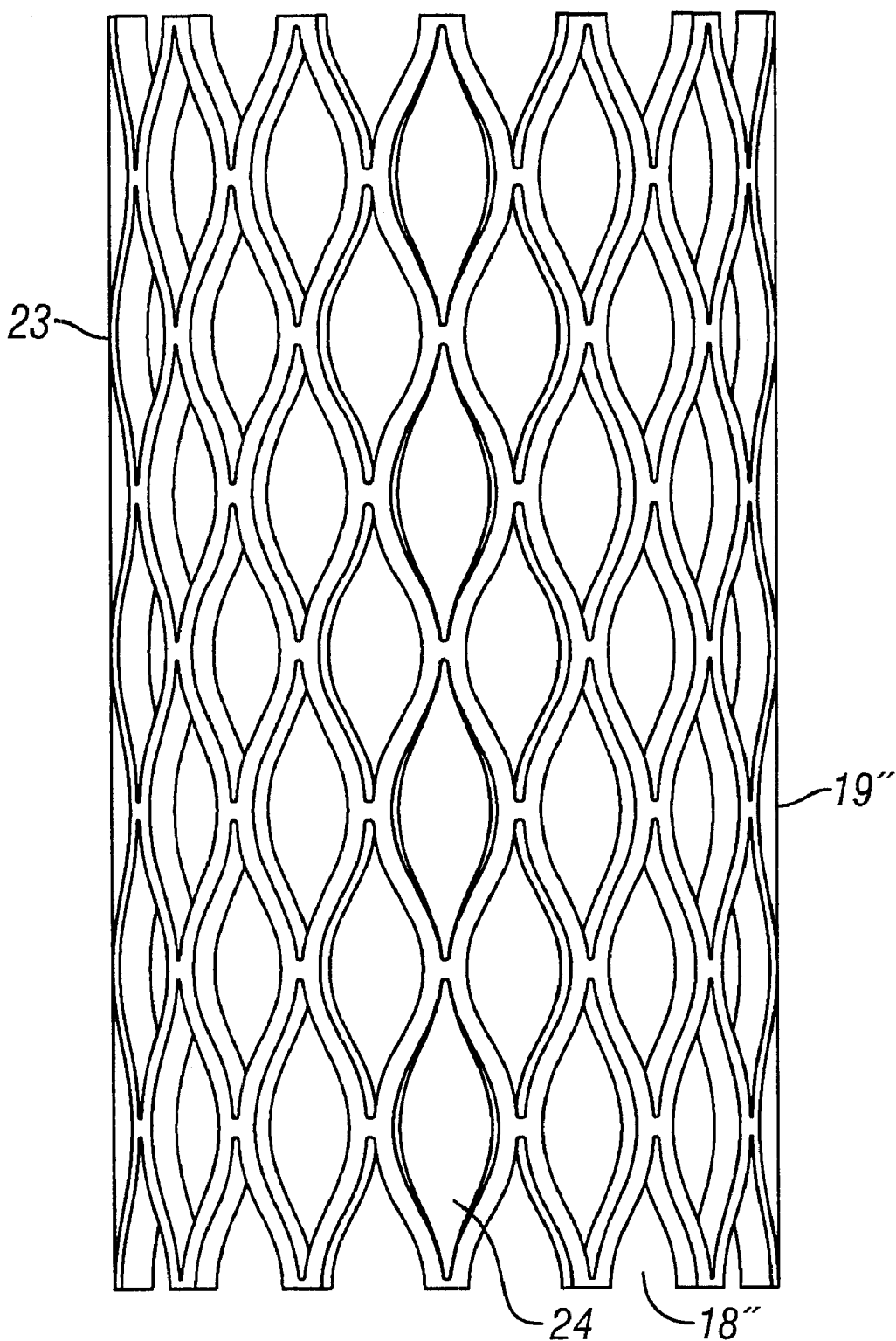
FIG. 3 depicts a bioresorbable stent with fenestrations in accordance with a preferred embodiment of the present invention.

In another preferred embodiment the stent 14 is made as described above except that a 24 carrier weave is used to produce a 48 strand device as shown in FIG. 2. Twenty-four monofilament pairs 36 are interwoven in a helical pattern on a round bar mandrel such that one-half of the monofilament pairs are wound clockwise and one-half are wound counter clockwise. Each monofilament pair intersects 15 the oppositely wound monofilament pairs in an alternating over-under pattern such that a tubular braid is made with crossing angles 16 between overlapping pairs of monofilaments in the longitudinal or axial direction (when the stent is in a non-compressed, resting position) of 100–150 degrees.

In yet another preferred embodiment a non-toxic radio-opaque marker is incorporated into the polymer blend prior to extruding the monofilaments used to weave the stent. Examples of suitable radio-opaque markers include, but are not limited to, barium sulfate and bismuth trioxide in a concentration of between approximately 5% to 30%.

Two important physical properties required of a self-expanding stent are compression resistance and self-expansion, or radial expansion, force. Compression resistance relates to the stent's ability to withstand the surrounding tissue's circumferential pressure. A stent with poor compression resistance will not be capable of maintaining patency. Self expansion force determines the stent's capacity to restore patency to a constricted lumen once inserted. The combination of self-expansion with resistance to compression are competing qualities and must be carefully considered when a stent is designed. The combination of polymer blending, processing, (including post-weaving annealing) and overall stent design and construction results in a superior stent 10, 14, 23 capable of surpassing the best performing metal stents found in the prior art.

Compression relaxation tests were conducted on an Instron test machine using a specially designed test fixture and a Mylar® collar. The test fixture consisted of a pair of freely rotating rollers separated by a 1 mm gap. The collar was a composite film of Mylar® and aluminum foil. Each 30 mm long stent was wrapped a 25 mm wide collar and the two mm ends of the collar were passed together through the gap between the rollers; a pulling force was applied to the ends of the collar, thus compressing the stent radially.

The raw data of crosshead displacement versus force was treated to obtain the constrained diameter versus force curve of the stent specimen. In this test method, the stent was subjected to two cycles of the following three sequential steps. First, the stent was compressed to 7 mm OD at a controlled speed. This portion of the test characterized the compression resistance of the stent. Second, the stent was held in the compressed state for a given duration, typically one minute. This portion of the test characterized the force decay or loss of recovery force. Third, the constraint on the stent was relaxed at a controlled rate. This portion of the test characterized the self-expansion force of the stent. The test may be conducted in air at room temperature, in water at a set temperature, or in an environmental chamber.

The 48 monofilament stent 14 in FIG. 2 can be compressed to a nominal diameter of approximately 6 mm to 7 mm and exerts a radial self-expansion force of approximately 18 N after release from the insertion tool. The fully deployed stent 14 expands to a diameter sufficient to restore or maintain patency in the patient. Returning the expanded stent to the fully compressed state requires approximately 25 N of circumferential pressure.

In another embodiment of the present invention, the 30 monofilament stent 10 can be compressed to a nominal diameter of approximately 6 mm to 7 mm which exerts a radial self-expansion force of approximately 25 N after release from the insertion tool. The fully deployed stent expands to a diameter sufficient to restore or maintain patency in the patient. Returning the fully expanded stent to the fully compressed state requires approximately 35 N of circumferential pressure. These high levels of radial expansion force and resistance to compression are benefits of the manufacturing process and stent design in accordance with the present invention. The all metal UroLume® stent manufactured by American Medical Systems of Minneapolis, Minn. has been tested to have an expansion force of 5 N at 7 mm and withstands 5 N of circumferential pressure at that diameter.

Furthermore, it was determined that bioresorbable stents 10, 14, 23 maybe manufactured in accordance with the present invention which are capable of retaining their initial self-expansion force and resistance to compression for a minimum of up to twelve weeks after deployment.

Figure 6:
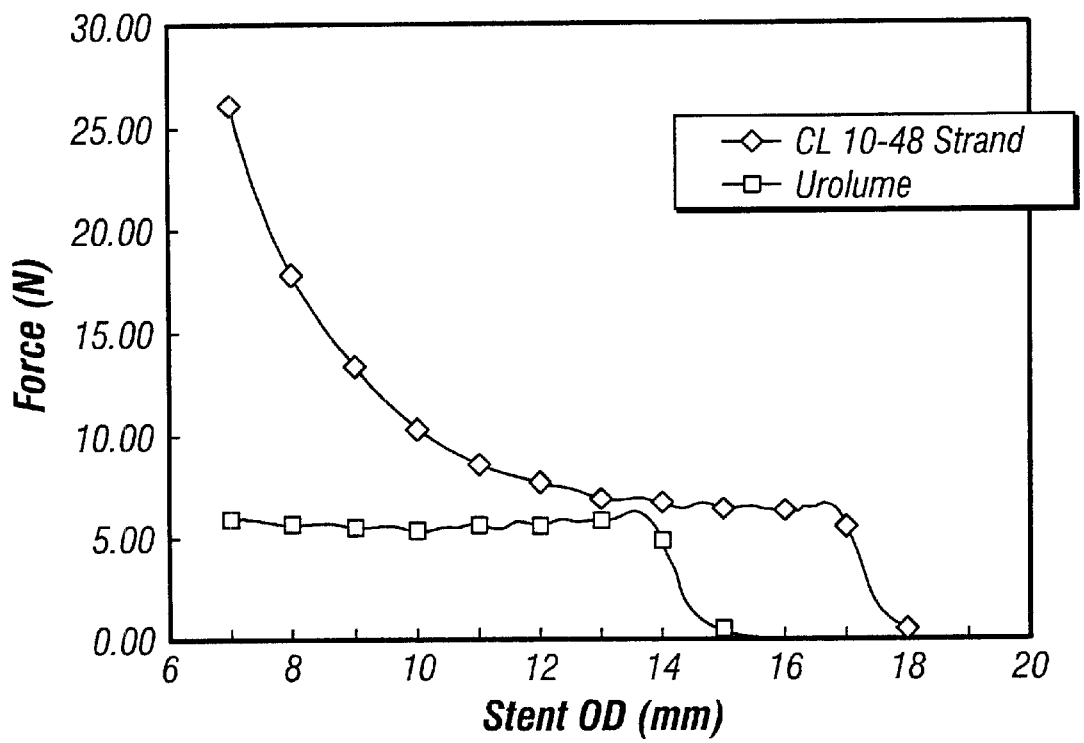
FIG. 6 graphically compares compression resistance of a 48 monofilament stent in accordance with a preferred embodiment of the present invention versus the UroLume® in a first compression cycle in air at ambient temperature.
Figure 7:
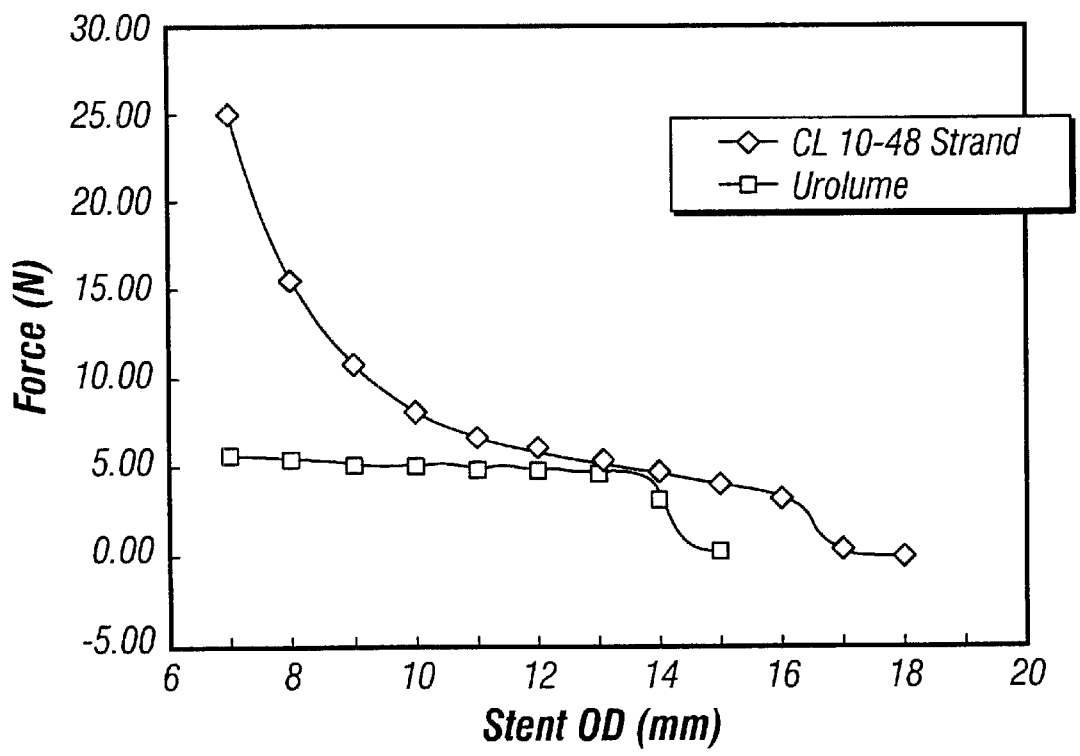
FIG. 7 graphically compares compression resistance of a 48 monofilament stent in accordance with a preferred embodiment of the present invention versus the UroLume® in a second compression cycle in air at ambient temperature with a one minute hold. The stents in this test were held in the fully compressed state for one minute during the first compression-expansion cycle.

FIG. 6 graphically compares the compression resistance of one embodiment of the present invention (designated CL10-48Strand) with the all metal urethral stent marketed by American Medical Systems under the trademark UroLume®. As illustrated, the present invention demonstrates superior compression resistance throughout the entire range of stent outer diameters (OD). Each stent was subjected to two rounds of compression and expansion to simulate conditions during actual use. The starting point in these two rounds of compression and expansion represents the stent in resting state prior to insertion into the application device. The first compression represents the forces used to compress the device into the applicator. The first expansion and the second compression simulate conditions exerted by and on the stent following release from the applicator and in situ circumferential pressures, respectively. The maximum compression resistance of the UroLume® at 7 mm was 6 N compared with 26 N at 7 mm for the stent made in accordance with the present invention. FIG. 7 compares the same two stents subjected to a second compression test. Similar results were obtained.

Figure 8:
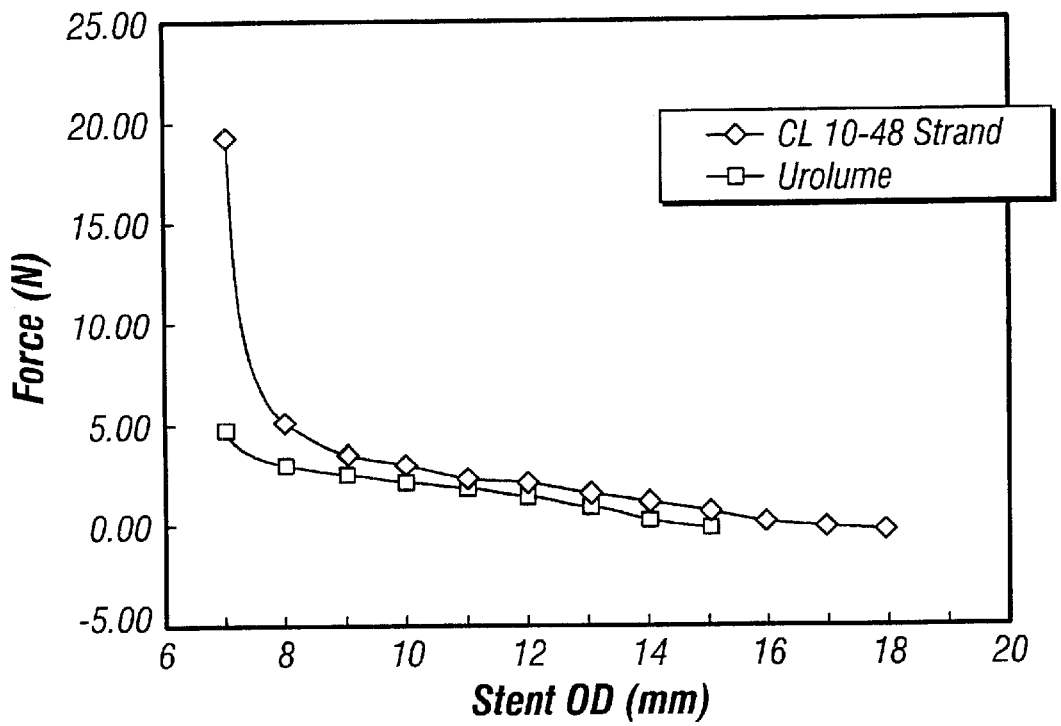
FIG. 8 graphically compares the self expansion force of a 48 monofilament stent in accordance with a preferred embodiment of the present invention versus the UroLume® in a first compression and expansion cycle in air at ambient temperature with a one minute hold during the first cycle.
Figure 9:
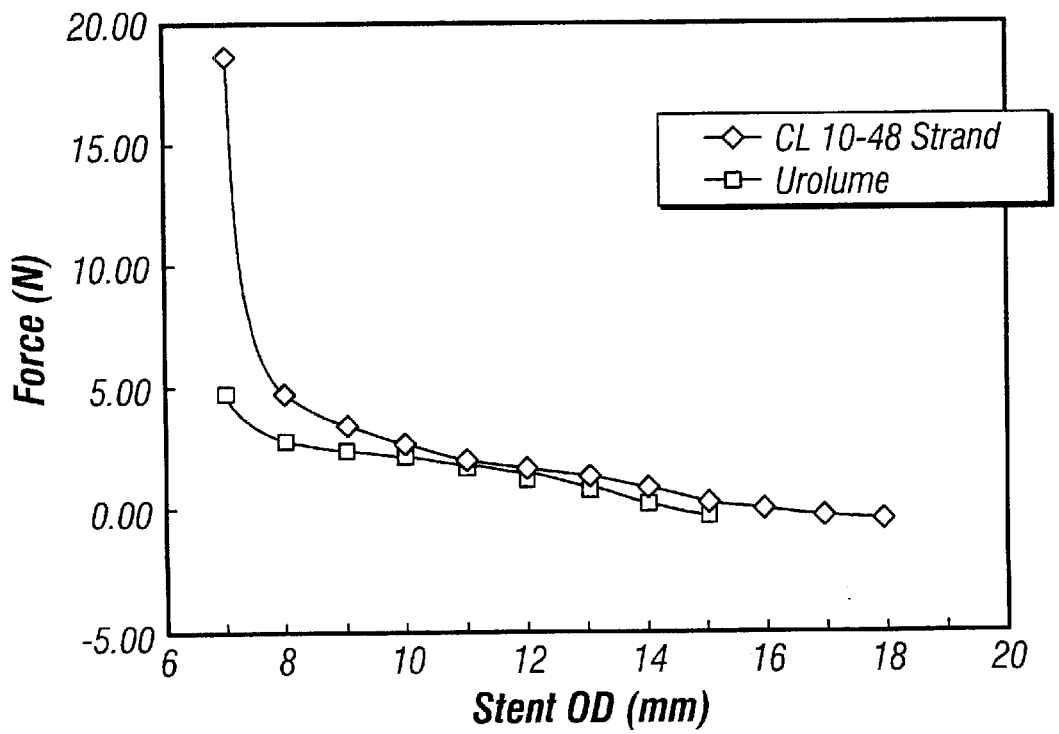
FIG. 9 graphically compares self expansion force of a 48 monofilament stent in accordance with a preferred embodiment of the present invention versus the UroLume® in a second compression and expansion cycle in air at ambient temperature with a one minute hold during each cycle.

FIGS. 8 and 9 depict the relative self expansion forces of the UroLume® stent and the 48 strand embodiment of the present invention during the first and second expansion cycles, respectively. At every corresponding diameter over the entire range of both tests the 48 monofilament, polymeric blend of the present invention demonstrated self expansion forces greater than or equal to that of the all metal UroLume® stent.

Figure 10:
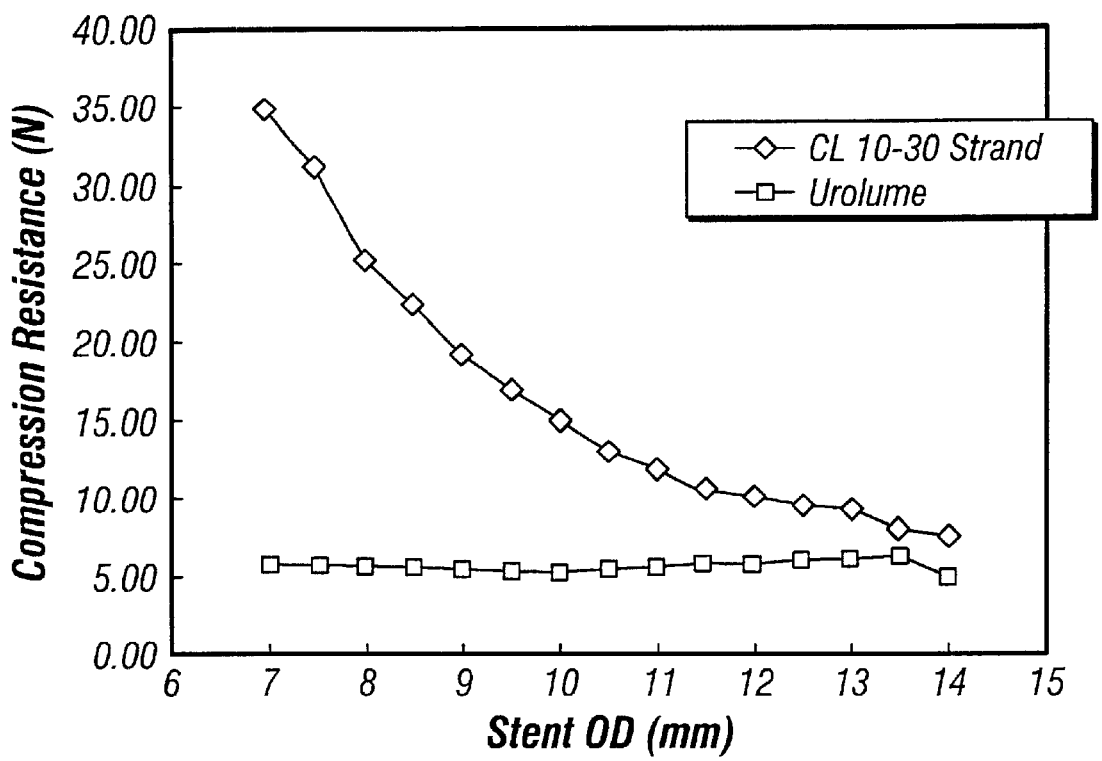
FIG. 10 graphically compares compression resistance of a 30 monofilament stent in accordance with a preferred embodiment of the present invention versus the UroLume® in a first compression cycle in air at ambient temperature.
Figure 11:
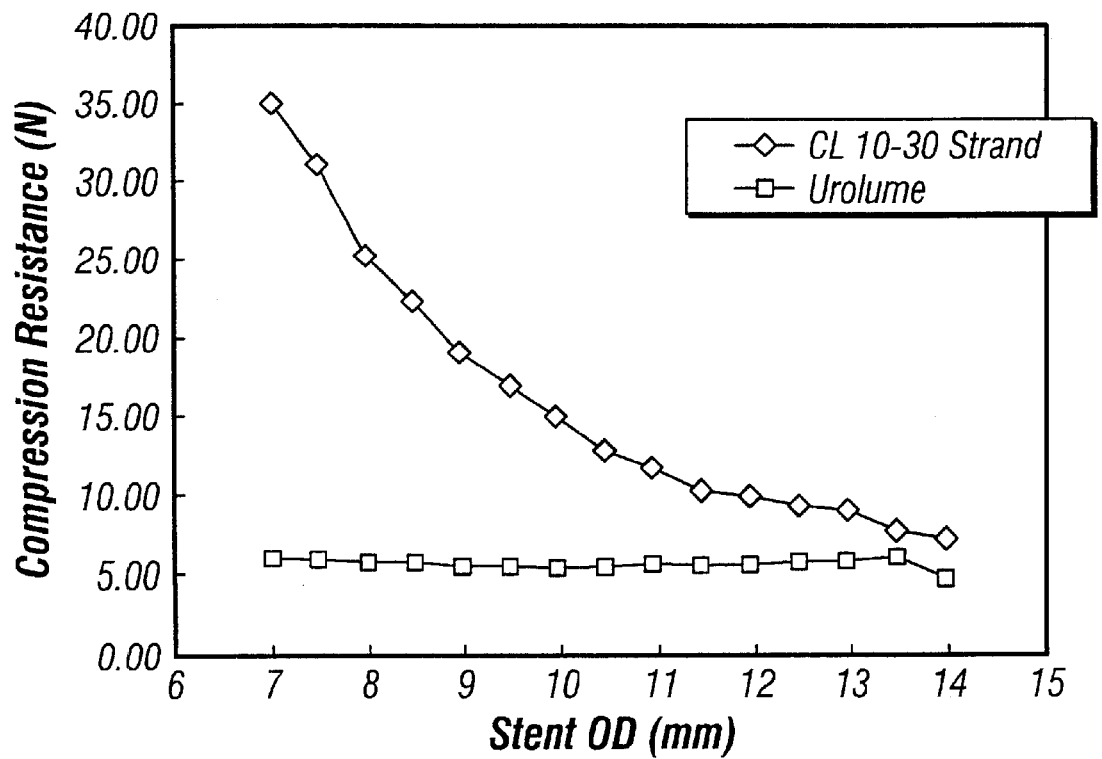
FIG. 11 graphically compares compression resistance of a 30 monofilament stent in accordance with a preferred embodiment of the present invention versus the UroLume® in a second compression and expansion cycle in air at ambient temperature with a one minute hold during the first cycle.

FIG. 10 graphically compares the compression resistance of another embodiment of the present invention (designated CL10-30Strand) with the all metal urethral stent marketed by American Medical Systems under the trade mark UroLume®. As illustrated, the present invention demonstrates superior compression resistance throughout the entire range of stent outer diameters (OD). The maximum compression resistance of the UroLume® at 7 mm was 6 N compared with 35 N at 7 mm for the present invention. FIG. 11 compares the same two stents subjected to a second round of compression tests; similar results were obtained.

Figure 12:
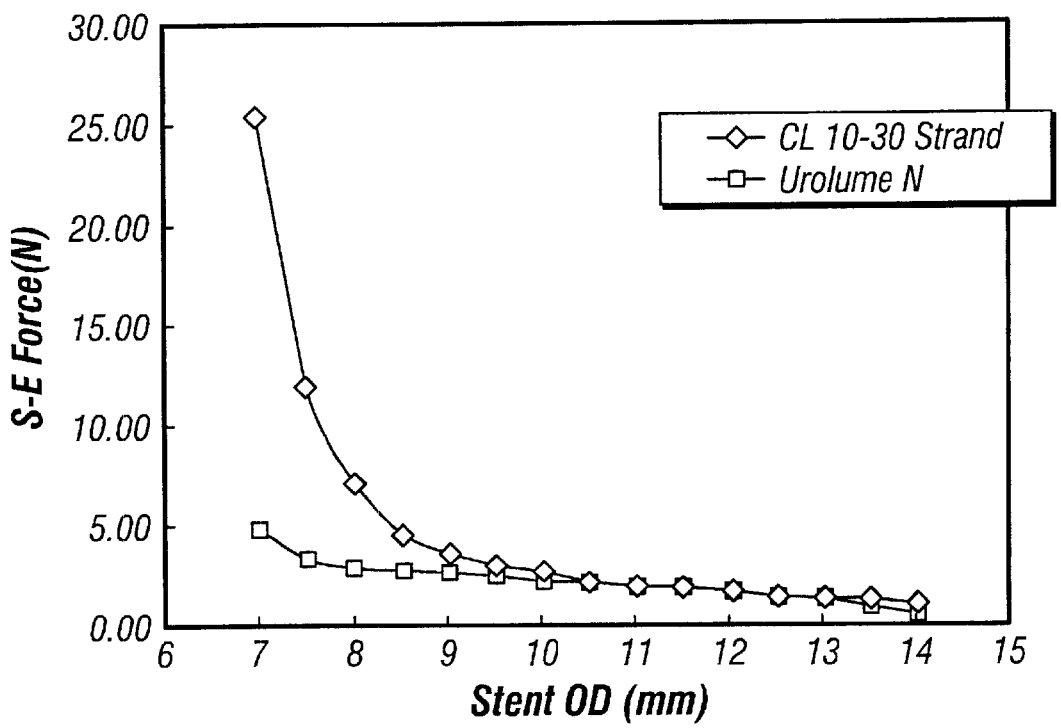
FIG. 12 graphically compares self expansion force of a 30 monofilament stent in accordance with a preferred embodiment of the present invention versus the UroLume® in a first compression and expansion cycle in air at ambient temperature with a one minute hold.
Figure 13:
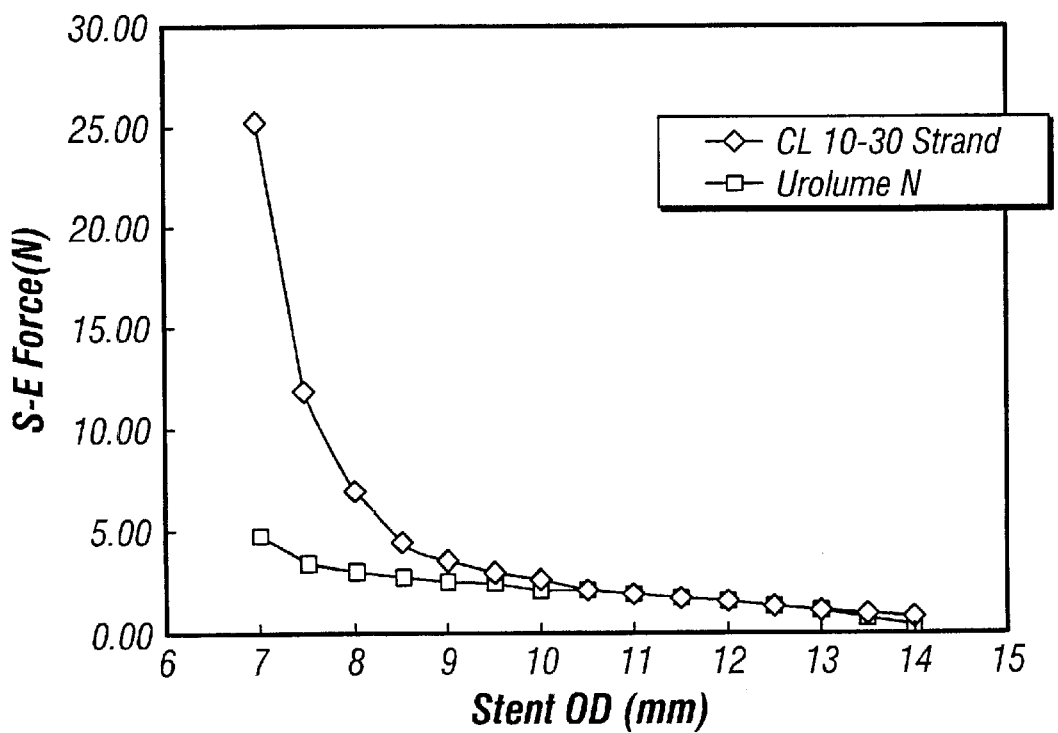
FIG. 13 graphically compares self expansion force of a 30 monofilament stent in accordance with a preferred embodiment of the present invention versus the UroLume® in a second compression and expansion cycle in air at ambient temperature with a one minute hold during each cycle.

FIGS. 12 and 13 depict the relative self expansion forces of the UroLume® stent and the 30 monofilament embodiment made in accordance with the present invention. The 30 monofilament, polymeric blend demonstrated self expansion forces greater than or equal to that of the all metal UroLume® stent throughout the entire OD range during both the first and second expansion cycles.

From the foregoing description, one skilled in the art can readily ascertain the essential characteristics of the invention and, without departing from the spirit and scope thereof, can adapt the invention to various usages and conditions. Changes in the form and substitution of equivalents are contemplated as circumstances may suggest or render expedient, and although specific terms have been employed herein, they are intended in a descriptive sense and not for purposes of limitation. Furthermore, any theories attempting to explain the mechanism of actions have been advanced merely to aid in the understanding of the invention and are not intended as limitations, the purview of the invention being delineated by the following claims.

What is claimed is:

1. A method for producing a stent comprising:
   a) blending at least two bioresorbable, bio-compatible homo-polymers in a predetermined ratio to form a blend;
   b) producing a monofilament from said blend by an extrusion process, said monofilament having a diameter between approximately 0.145 mm and 0.6 mm;
   c) extruding the monofilaments to a draw ratio of between approximately 3.5 to 5.5;
   d) braiding the monofilaments into a substantially helical weave forming a tubular-shaped device;
   e) annealing said tubular-shaped device at a temperature between the glass transition temperature and melting temperature of the blended polymers for between approximately five minutes and 18 hours.

2. The method of claim 1, wherein said blend of at least two homo-polymers is a blend of two polymers.

3. The method of claim 2, wherein said homo-polymers are poly-L-lactide and poly-ε-caprolactone.

4. The method of claim 1, wherein said predetermined ratio is in between approximately 80:10 to 99:1.

5. The method of claim 4, wherein said ratio is approximately 90:10.

6. The method of claim 1, wherein said diameter of said monofilament is between approximately 0.35 mm and 0.45 mm.

7. The method of claim 1, wherein said draw ratio is approximately 4.5.

8. The method of claim 1, wherein said annealing step further comprises heating the stent to 90° C. for 1 hour followed by a second, uninterrupted heating cycle at 140° C. for two hours under an inert atmosphere.

9. The method of claim 1, wherein said braiding step includes winding thirty monofilaments in a manner such that one-half of the monofilaments are wound clockwise and one-half are wound counter clockwise and wherein each clockwise monofilament intersects the counter-clockwise monofilaments in an alternating over-under pattern such that a tubular braid is made with crossing angles between overlapping monofilaments in the longitudinal or axial direction of 100–150 degrees when the stent is in a substantially non-compressed state.

10. The method of claim 1, wherein said braiding step includes winding twenty-four pairs of monofilaments in a manner such that one-half of the monofilament pairs are wound clockwise and one-half are wound counter clockwise such that each clockwise monofilament pair intersects sequential counter-clockwise monofilament pairs in an alternating over-under pattern such that a tubular braid is made with crossing angles between overlapping pairs of monofilaments in the longitudinal or axial direction of 100–150 degrees when the stent is in a substantially non-compressed state.

11. The method of claim 1, further comprising the step of adding a radio-opaque marker to said bioresorbable stent.

12. The method of claim 1 wherein said radio-opaque marker is composed of a member selected from the group consisting of barium sulfate and bismuth trioxide in a concentration of between approximately 5% and 30%.

13. A bioresorbable stent made in accordance with the methods of claim 12.

* * * * *